United States Patent
Khudoley (12) 
(10) Patent No.: US 8,683,639 B2
(45) Date of Patent: Apr. 1, 2014

(54) MECHANICAL TOOTHBRUSH AND DRIVE MECHANISM THEREFOR (EMBODIMENTS)

(75) Inventor: Vladimir Nikolaevich Khudoley, Timiryazevskoe (RU)

(73) Assignee: Diastam Ltd, Tomsk (RU)

( * ) Notice: Subject to any disclaimer, the term of this patent is extended or adjusted under 35 U.S.C. 154(b) by 227 days.

(21) Appl. No.: 13/138,943

(22) PCT Filed: Apr. 26, 2010

(86) PCT No.: PCT/RU2010/000198
§ 371 (c)(1),
(2), (4) Date: Oct. 28, 2011

(87) PCT Pub. No.: WO2010/128894
PCT Pub. Date: Nov. 11, 2010

(65) Prior Publication Data
US 2012/0042459 A1    Feb. 23, 2012

(30) Foreign Application Priority Data

May 4, 2009  (RU) ................................ 2009117006

(51) Int. Cl.
*A61C 17/26*    (2006.01)
*A61C 17/34*    (2006.01)

(52) U.S. Cl.
USPC .............................................. 15/23; 15/22.1

(58) Field of Classification Search
USPC ...................................... 15/22.1, 22.4, 23, 28
See application file for complete search history.

(56) References Cited

U.S. PATENT DOCUMENTS

| | | | | |
|---|---|---|---|---|
| 1,517,320 A * | 12/1924 | Stoddart | ........................ | 15/22.1 |
| 5,077,855 A * | 1/1992 | Ambasz | ........................ | 15/22.1 |
| 5,259,083 A * | 11/1993 | Stansbury, Jr. | .................. | 15/22.1 |
| 5,778,474 A * | 7/1998 | Shek | .............................. | 15/22.1 |
| 8,032,964 B2 * | 10/2011 | Farrell et al. | ................... | 15/22.1 |

FOREIGN PATENT DOCUMENTS

| | | |
|---|---|---|
| CN | 2808083 | 8/2006 |
| CN | 201044776 | 4/2008 |
| DE | 3544256 | * 6/1987 |
| RU | 2240714 | 11/2004 |
| SU | 1808297 | 4/1993 |
| WO | WO 84/02833 | 8/1984 |

* cited by examiner

*Primary Examiner* — Mark Spisich
(74) *Attorney, Agent, or Firm* — Aleksandr Smushkovich (57) ABSTRACT

A toothbrush is proposed that includes a handle, a neck, and a head arranged along a longitudinal axis thereof. The head is open on one side and functions as a protective screen. Movable ring-shaped holders with bristles radially secured thereon are mounted in the head. The holders' butt ends are joined to one another and to the protective screen by movable seals forming a hermetical body to protect the toothbrush's drive mechanism from penetration of water and toothpaste. Two design options allow the holders for accomplishing-angular oscillatory movements, or -rotating in opposite directions about the longitudinal axis, thus ensuring bristles' movements from top to bottom along the user's teeth. The proposed design ensures a high cleaning effectiveness, water tightness, and compensation of a reactive torque of the toothbrush, which extends the service life of the toothbrush and facilitates the use thereof.

5 Claims, 5 Drawing Sheets

MECHANICAL TOOTHBRUSH AND DRIVE MECHANISM THEREFOR (EMBODIMENTS)

CROSS-REFERENCE TO RELATED APPLICATIONS

This application is a U.S. national stage application of a PCT application PCT/RU2010/000198 filed on 26 Aug. 2010, published as WO2010/128894, whose disclosure is incorporated herein in its entirety by reference, which PCT application claims priority of a Russian application RU2009117006 filed on 4 May 2009.

FIELD OF THE INVENTION

The invention relates to medical technology, specifically to oral care, particularly to mechanical toothbrushes powered preferably by a small battery.

BACKGROUND OF THE INVENTION

Advantages of tooth brushing with the usage of mechanical toothbrushes are well-known. Mechanized (also called electrical) toothbrushes usually comprise typical units: a handle with a motor, a neck and a head with movable bristle holders, and a mechanism, driving the bristle holders into movement, which units are successively arranged along the longitudinal axis of the brush.

Mechanical toothbrushes with bristle holders rotating along the longitudinal axis of the toothbrush have a simplest design (U.S. Pat. No. 4,163,300). A head of such a toothbrush is made as a protective screen opened on one side, whereon a movable bristle holder is arranged. The movable bristle holder is produced as a rotating shaft with radially extended bristles or bunches of bristles, forming a brush, which bristles are fixed along the whole shaft. The rotating shaft is directly joined with a motor shaft. The main deficiency of such head is that, during rotation of the bristle holder, a reactive torque appears in the handle, which torque should be compensated with a handle held in the fingers that makes the toothbrush very inconvenient in usage.

This deficiency is absent in the heads of other toothbrushes (U.S. Pat. No. 5,864,911), having two parallel elastic brush holders rotating in the opposite directions, which brush holders are installed inside the protective screen. Shafts of the holders are joined with a motor by flexible shafts through a system of tooth wheels. The toothbrush is intended for simultaneous tooth brushing on both sides. For this purpose, bushes are mounted at some distance from each other with a possibility of change of this distance at the expense of the elastic holders. The deficiency of the toothbrush is that it is possible to clean a separately standing tooth effectively, but during the cleaning a row of teeth the contact between the bristle surface and the teeth surface is not tight enough, especially at those sections of the jaw, which have an arched form.

A mechanized toothbrush with holders rotating along the longitudinal axis and intended for tooth brushing on one side is also known (EP0488971). The toothbrush holders are also formed as two parallel shafts with a radial arrangement of bristles. The holders are arranged in relation to each other at a distance slightly exceeding the length of the bristles in such a way that the bristles of the holders overlap each other. The holders rotate in the opposite directions driven by a set of gear teeth arranged together with a motor in the handle. A problem of hermetical sealing of the drive is solved in such toothbrushes, the water tightness is provided by sealing the rotating shafts.

The main deficiency of the toothbrush as well as of all analogous toothbrushes with a brush-shaped bristle holder is the following. A rod-shaped holder of the toothbrush has a very high density of bristles immediately near the rod to provide a sufficient density of the brushes near their ends. Food residues and contaminants caught by bristles under the action of centripetal forces are accumulated between the bristles in the area of increased density of bristles. It is very difficult to wash such a toothbrush. It becomes unsuitable for usage quickly because of the crossing bristles. This significant deficiency didn't allow for widespread use of such toothbrushes.

There is known a toothbrush without a mechanical drive, in which a manual longitudinal displacement of the toothbrush is converted into a rotational movement of bristle holders (RU2240714). The toothbrush contains numerous rotary bristle holders mechanically joined for moving together with the handle. Each such holder is formed as a wheel with radially exposed bristles. The wheels are installed on axles capable of rotation. The axles are disposed in a plane parallel to the plane of contact with the teeth and at an angle to the longitudinal axis of the toothbrush. This angle is in the range of 15-75 degrees. For such an inclined arrangement of the wheel axles in relation to the toothbrush movement, friction of the bristles with the teeth leads to rotation of the wheels, and an ordinary cleaning movement 'from-side-to-side' creates a secondary effect of tooth brushing 'from-top-to-bottom'. This toothbrush relates to manual ones and doesn't have a drive mechanism of bristle holders, and in this regard there is no necessity in hermetic sealing.

There are known mechanical toothbrushes with an oscillatory or rotational movement of bristle holders of a different shape about an axis perpendicular to the plane of the brushing part of the toothbrush (for example, RU2270638, WO2004/080330, WO 2004093718, etc.).

Toothbrushes with a reciprocal movement of holders along the longitudinal axis (WO03/103531) are also known. For increase of the cleaning efficacy, several holders oscillating in an anti-phase are used, as shown in FIG. 6B in Patent RU2318471. Such toothbrushes have a low cleaning efficiency of tooth brushing conditioned by the movement of bristles across the teeth. It is known, that the best results are achieved during the tooth brushing by moving the bristles from top to bottom that helps removing food residues remaining in the slots between neighbour teeth, therefore the mechanical movement in electrical toothbrushes is an object of modern inventive and designing activity.

For the last years many various types of mechanical toothbrushes with a complicated movement of bristle holders in different planes have appeared (U.S. Pat. No. 5,070,567, RU 2300344 and etc.) However, the most effective tooth brushing has been achieved therein with the aid of more complicated, expensive, and inefficient drive mechanisms.

There have appeared mechanical toothbrushes, having bristles, which imitate a movement produced by the hand brushing made from-top-to-bottom (RU 2314775, FIGS. 2 and 3). Three bristle holders are made therein in the form of blocks projecting out of the toothbrush head body opened on one side. The body performs a function of the protective screen. The holders are capable of accomplishing angular oscillatory movements about an axle mounted in the head body parallel to the longitudinal axis of the brush. The neighbour holders carry out a movement in the opposite directions. This toothbrush is considered a closest related art device, herein further called a 'prototype'.

The prototype brush includes bristle holders having cams mounted in the lower parts thereof and a drive mechanism of a linear type, having a head area with a curved cam slot arranged therein, which cam slot interacts with the cams. In another embodiment of the prototype, a drive shaft is curved in the area of the brush head, while forming a cam area, and a lower end of each holder is made with a slot interacting with this curved cam area of the drive shaft.

In such toothbrushes there is a typical problem of hermetic sealing of the drive mechanism against water and toothpaste, which lead to failures of the toothbrush in case of penetration of water and toothpaste inside the brush head. The linear drive used in the toothbrush is not rigid enough and limits the transmission of power required for an effective tooth brushing. Besides, the drive mechanism limits a turn angle of the holders, and the resultant movement is not sufficient for an effective tooth brushing. The projecting parts of the bristle holders, moving towards each other, create a danger of pinching of soft tissues of the oral cavity. The presence of three holders moving in the opposite directions doesn't provide a proper compensation of the reactive torque, which is passed to the consumer's fingers.

Therefore, the task of creating a mechanized toothbrush with parameters desirable by the consumer, including simplicity and reasonable costs, still remains actual.

BRIEF DESCRIPTION OF THE INVENTION

A primary aim of the present invention is the provision of hermetic sealing of the toothbrush drive, compensation of the reactive moment, and improvement of safety of using the toothbrush. To achieve the aforesaid aim, the inventive mechanized toothbrush, similarly to the prototype, includes the following units arranged along a longitudinal axis of the toothbrush: a handle containing a motor; a neck; and a head; a drive mechanism arranged within the handle, neck, and head. The head is made in the form of a protective screen opened on one side, whereon a number of movable bristle holders are mounted, which bristle holders are driven by the drive mechanism. The protective screen has butt ends. The bristle holders are made with a capability of the angular displacement in opposite directions about a longitudinal axis of the toothbrush.

Distinct from the prototype, the bristle holders, the number of which is even, are made in the form of separate rings with a radial arrangement of bristles. The rings, having butt ends, are arranged along the longitudinal axis and joined with the butt ends to one another and with the butt ends of the protective screen by means of movable seals in such a way that they form a hermetically sealed body for the drive mechanism.

The inventive mechanized toothbrush can be made in two design options: with an intermittent angular displacement of holders, being an oscillatory movement; and with a continuous angular displacement of holders, being a rotational movement.

In the first design option, the bristle holders are made with a capability of an angular oscillatory movement, while the bristles are mounted only in the part of surface of the ring-shaped holders turned to the open side of the protective screen. The drive mechanism is made to provide angular oscillations. The drive mechanism of an angular oscillatory movement for the first option comprises a crank joined with an output shaft of the motor. The crank has two elbows. Two forks, joined with two coaxial shafts (inner and outer) are arranged in the head along the longitudinal axis, and joined with both the crank elbows. Each of the coaxial shafts has radial fingers which are engaged with the bristle holders in the next but one order. The fingers of the inner shaft pass to corresponding bristle holders through arched holes on the side surface of the outer shaft.

In the second design option, the bristle holders are made with a capability of continuous angular displacement, while the bristles are mounted on the entire cylindrical surface of the ring-shaped holders. The drive mechanism is a rotating drive. In one of possible embodiments of the second design option, the drive mechanism comprises two parallel shafts joined with a motor shaft by means of tooth gears providing rotation of the parallel shafts in opposite directions. On the inner surface of each of the ring-shaped bristle holders there are gear teeth of inner engagement. A plurality of pinions are mounted on each of the parallel shafts in the area adjacent to the corresponding bristle holders in such a way that the pinions of a first shaft engage with the gear teeth of the even bristle holders, and the pinions of the second shaft engage with the gear teeth of the uneven bristle holders.

It should be noted that the drive design options described herein above do not deplete all possible embodiments of realization of the mechanical drives for the angular oscillatory movement and rotational movement.

BRIEF DESCRIPTION OF DRAWINGS

The invention is illustrated by graphic materials, wherein:

FIGS. 1-4 illustrate a toothbrush with an oscillatory movement of bristle holders, according to an embodiment of the present invention. In particular.

FIGS. 5-7 illustrate the toothbrush with a rotational movement of bristle holders, according to another embodiment of the present invention. In particular.

PREFERRED EMBODIMENTS OF THE PRESENT INVENTION

While the invention may be susceptible to embodiment in different forms, there are described in detail herein below, specific embodiments of the present invention, with the understanding that the present disclosure is to be considered an exemplification of the principles of the invention, and is not intended to limit the invention to that as illustrated and described herein.

Let's consider the toothbrush shown in FIGS. 1-4. The toothbrush has a longitudinal axis, and comprises a handle 1, a cylindrical neck 2, and a head 3 arranged successively one by one along the longitudinal axis. There is a motor 4 mounted in the handle 1. The motor 4 can be exemplarily powered by a suitable battery. The head 3 has a protective screen 5 with one open side. The screen 5 is rigidly joined to the neck 2 by butt ends 6 and 7. The toothbrush comprises a number of ring-shaped bristle holders 8 retaining bristles 9. The bristle holders 8 are installed in the head 3. The bristle holders 8 include arched parts turned to the open side of the protective screen 5. The bristles 9 are radially extended outwards from the bristle holders 8 and mounted only on the arched parts.

Provided that the bristle density in its ends is normal for cleaning, the bristle density near the surface of bristle holders 8 is far less than in the above-described related art brush-shaped toothbrushes, therefore the bristles in the proposed toothbrush will accumulate much less food residue and thus blocked with dirt to a lesser extent, which is an important advantage of the present invention.

According to the invention, the number of the bristle holders 8 must be even, because only in this case the holders 8 moving in the opposite directions will provide full compensation of the reactive moment, and which facilitates the use of the toothbrush. The bristle holders are arranged along the longitudinal axis of the brush and are joined to one another by butt ends, forming a movable seal.

Figures 1, 2:
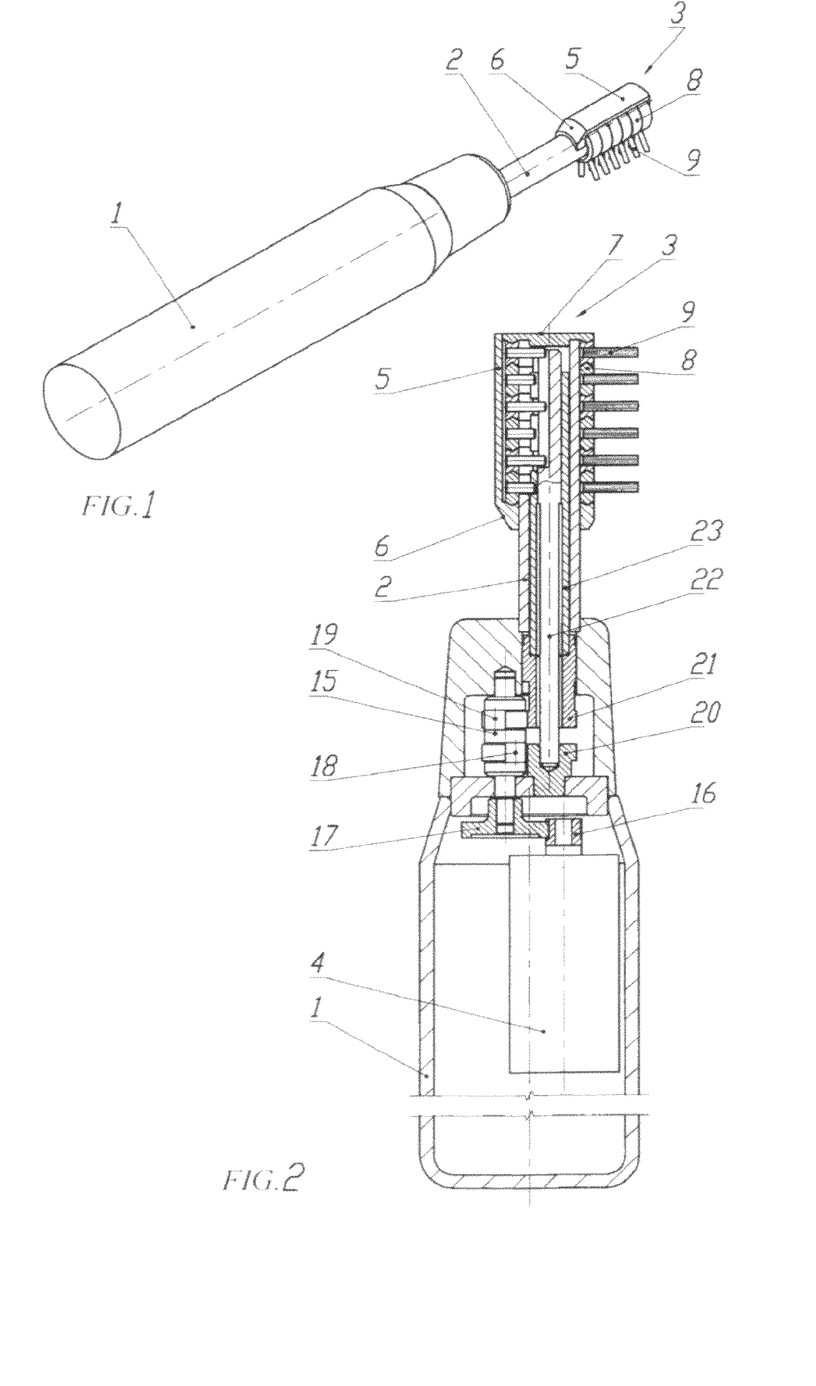
FIG. 1 is an overall view of the toothbrush.
FIG. 2 is a cross-section view of the toothbrush along the longitudinal axis.
Figure 3:
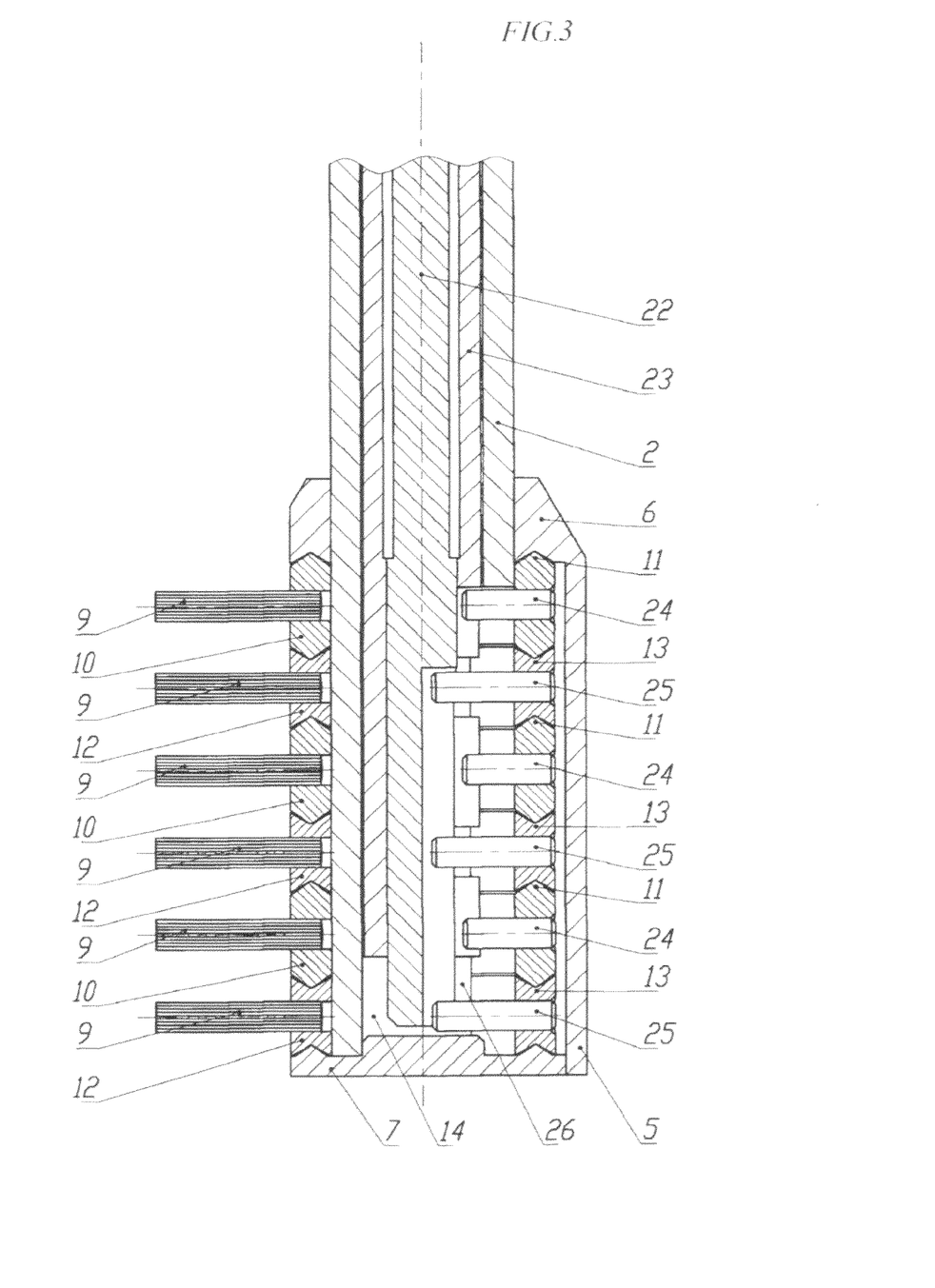
FIG. 3 is a cross-section view of the toothbrush head shown separately in a large scale.

In the specific embodiment illustrated in FIGS. 2-3 the movable seals are configured as seals of a "dovetail" type. The bristle holders 8 consist of uneven (when counted from the handle 1) holders 10 and even (when counted from the handle 1) holders 12. The butt ends of the holders 10 are made with triangle (or having a veed-like shape) projecting edges 11, and the butt ends of the holders 12 are made with deepening edges 13 of the corresponding triangular profile. The holders 10 with veed-like seal edges 11 are situated adjacently with the holders 12 with deepening seal edges 13 (i.e. any holder 10 is neighboring only with one or two holder(s) 12 and vice-versa). In other words, the veed-like seal edges 11 form a movable seal by mating with the deepening seal edges 13 intermitting therewith. The ending (boundary) holders 10 and 12 are sealingly connected with the butt ends 6 and 7 of the protective screen 5 in the same manner, i.e. by means of the triangle veed-deepening profiles.

Consequently, the ring-shaped holders 8 form a hermetic cavity 14 in the head 3 with the aid of the seal edges 11 and 13 together with the neck 2 and the butt ends 6 and 7. Driving elements for rotating the holders 8 are arranged in this cavity 14. Thanks to the hermetic sealing, water and toothpaste do not penetrate inside the head 3, and the drive elements operate in favorable conditions that extend the service life of the toothbrush.

According to one preferred embodiment of the first design option, the inventive toothbrush comprises a drive of angular oscillatory movement, which drive includes a crank 15 driven by the motor 4 via a tooth-gear pair 16-17 (or a tooth wheel 16 and a tooth wheel 17, see FIGS. 2 and 4); the motor 4 and the tooth-gear pair 16-17 are encapsulated into the handle 1. In this embodiment, the crank 15 has two elbows 18 and 19.

The drive includes forks 20 and 21 joined with the elbows 18 and 19. The fork 20 is joined with an inner shaft 22 extending along the longitudinal axis. The fork 21 is joined with a hollow outer shaft 23 enclosing the inner shaft 22 coaxially disposed within the outer shaft 23. The outer shaft 23 includes a plurality of arched holes 26 (FIG. 4) having predetermined lengths.

Figure 4:
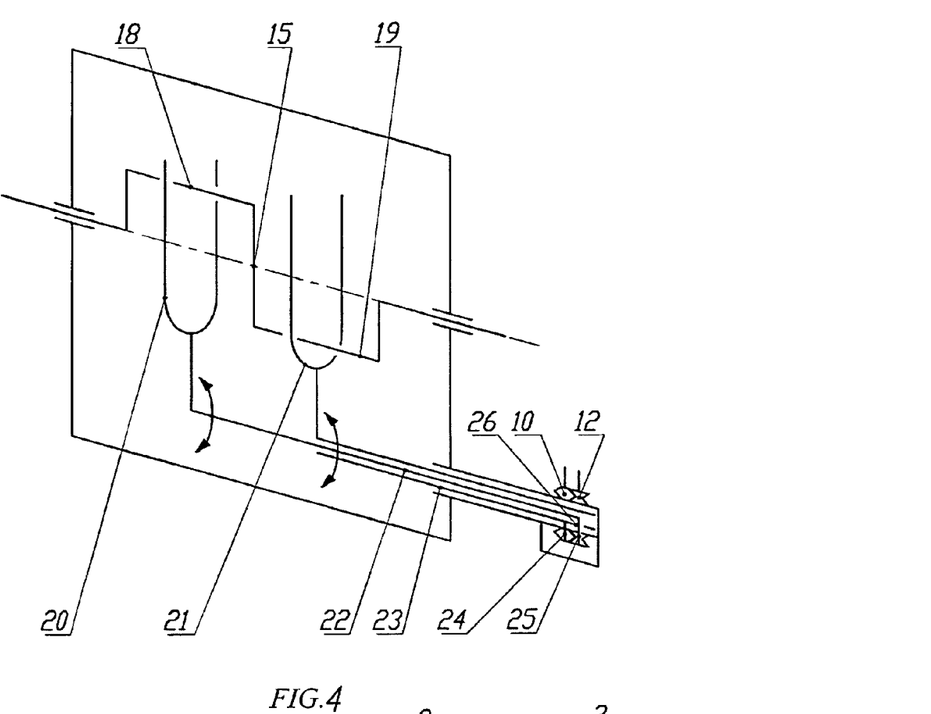
FIG. 4 is a schematic view of one of possible embodiments of the mechanical drive with angular oscillatory movement of bristle holders.

The outer shaft 23 is made with fingers 24 engage with the uneven ring-shaped holders 10 (see FIGS. 3 and 4). The inner shaft 22 has fingers 25 which pass through the arched holes 26 and engage with the even ring-shaped holders 12. The length of each arched hole 26 must provide a capability of turning the holders 12 at a maximal predetermined angle.

The inventive toothbrush with an oscillatory movement of the ring-shaped holders operates in the following way. When the motor 4 is switched on, its output shaft rotates the tooth wheel 17 and the crank 15 through the tooth wheel 16. With the aid of the forks 20 and 21, the rotation of elbows 18 and 19 is transformed in an anti-phase oscillatory movement of the coaxial shafts 22 and 23. As the uneven bristle holders 10 are joined with the outer shaft 23 by the fingers 24, they all oscillate at every moment of time in one direction.

The even bristle holders 12 joined with the inner shaft 22 by means of the fingers 24 turn in the opposite direction at the same moment of time. Consequently, the neighbor ring-shaped bristle holders 10 and 12 perform angular displacements in the direction opposite to each other at every moment of time. During the movement of the toothbrush head with the user's hand in the longitudinal direction, the bristles, in relation to the user's teeth, will perform a successive movement from top to bottom, thus providing a movement optimal in terms of effectiveness of the teeth cleaning.

Figure 5:
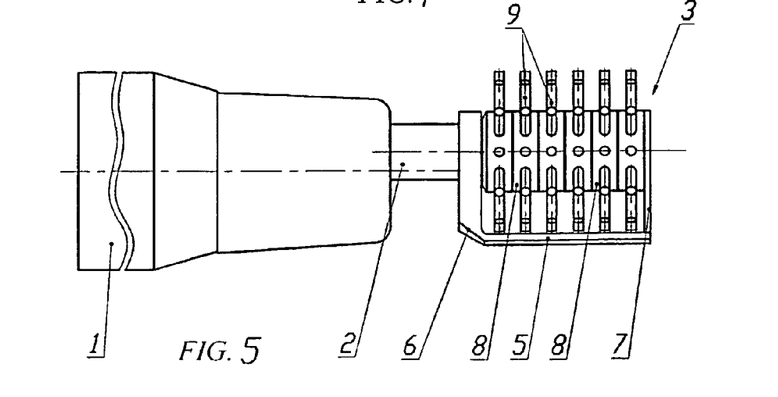
FIG. 5 is an overall view of the toothbrush.

With the same length of bristles, a preferred embodiment of the second design option of the toothbrush will have a slightly bigger radial size of the head because of the fact that the bristles are arranged on the whole perimeter of the ring-shaped holder. A similar toothbrush in the same proportions is depicted in FIG. 5. The toothbrush of this embodiment has a longitudinal axis, and also comprises a handle 1 with a motor (not shown in FIG), a cylindrical neck 2, and a head 3. The head 3 comprises a protective screen 5 with butt ends 6 and 7 (see FIGS. 5 and 6). The screen 5 is opened on one side. The screen 5 is rigidly joined on the neck 2 by the butt ends 6 and 7. The toothbrush comprises a number of ring-shaped bristle holders 8, subdivided into even holders 12 and uneven holders 10, which are mounted on the head 3 inside the screen 5.

Figure 6:
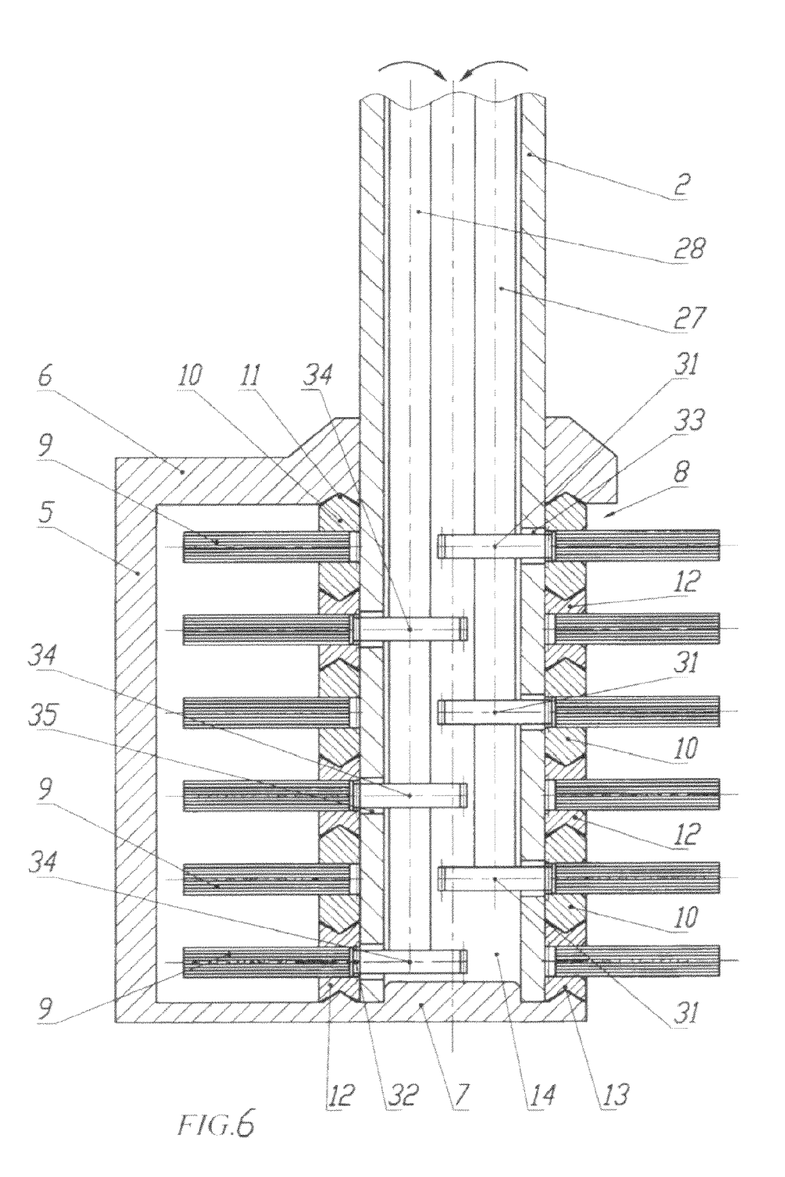
FIG. 6 is an axial cross-section view of the toothbrush head.

Bristles 9 are equally arranged on the whole surface of the ring-shaped holders 8 and extended outwards radially. Provided that the bristle density in its ends is normal, the bristle density near the surface of bristle holders 8 is far less than the one described in the related art toothbrushes, and it is much easier to wash.

The ring-shaped bristle holders 8 are arranged along the longitudinal axis and joined to one another with the aid of movable seals. A movable seal of any two neighbor bristle holders is also made here in the dovetail form, i.e. the uneven ring-shaped bristle holders 10 have veed-shaped edges 11 of a triangular cross-section at the butt ends that interfit with triangular deepenings 13 made at the butt ends of the even ring-shaped bristle holders 12.

The boundary ring-shaped holders 8 are mated with the butt ends 6 and 7 of the protective screen 5 by the same type of seal. As in the previous case, the ring-shaped holders 10 and 12 together with the above-described seals and the butt ends 6 and 7 of the protective screen 5 form a hermetic body 14, in which drive elements are arranged. For driving the bristle holders into rotation, the inner surface of all ring-shaped holders 8 is made in the form of tooth gear wheels 32 of the inner engagement.

The rotating drive of this embodiment of the toothbrush (see FIG. 7) comprises two parallel shafts 27 and 28, one of which is rotated directly by the output shaft of motor 4, and the other is through tooth gear wheels 29 and 30 in the opposite direction.

Figure 7:
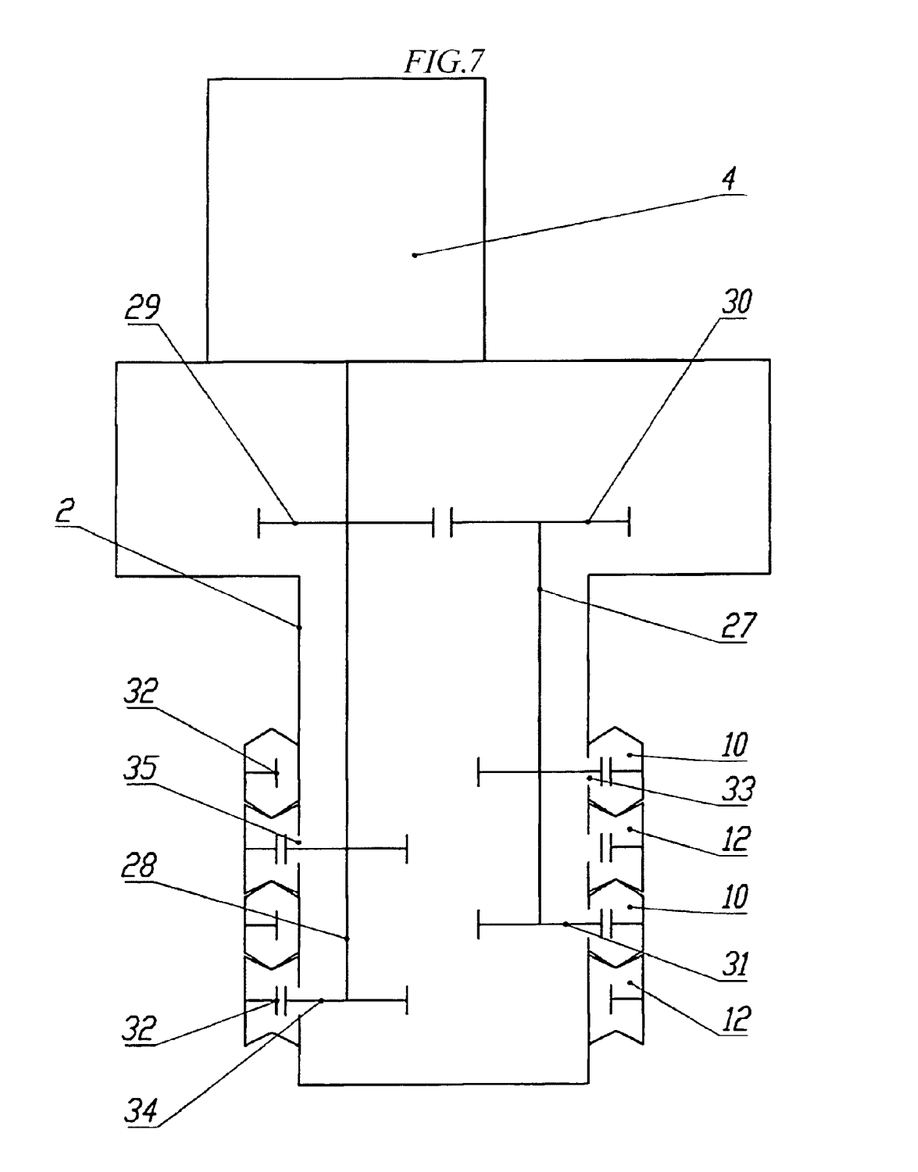
FIG. 7 is a schematic view of one of possible embodiments of a rotational drive for the bristle holders.

The rotating drive comprises pinions 31 fixed on the shaft 27 in the hermetic cavity 14 against the uneven holders 10. The pinions 31 engage with the gear wheels 32 of the uneven holders 10 through holes 33 made in the head 3. The rotating drive comprises pinions 34 fixed on the shaft 28 against the even holders 12. These pinions 34 engage with the gear wheels 32 of the even holders 12 through similar holes 35 made in the head 3.

This embodiment of the inventive toothbrush operates in the following way. When the motor 4 is switched on, the shafts 27 and 28 rotate in the opposite directions. The shaft 28 rotates all the even ring-shaped bristle holders 12 by means of the pinions 34. The shaft 27 rotates all the uneven ring-shaped holders 10 through the pinions 31 in the opposite direction.

Consequently, the neighbor rings of bristle holders 10 rotate in the opposite directions. The screen 5 encloses an opposite inoperative surface of the head 3 and protects soft tissues of the user's oral cavity from exposure to the bristles 9. During a manual movement of the head 3 along the user's teeth, each tooth is exposed to successive cleaning movements of the bristles from top to bottom along the tooth.

In other words, the most effective movement of bristles in terms of quality of tooth brushing is accomplished. All details and elements of the drive mechanism of the bristle holders are sealed reliably and in a rather simple way, and are not exposed to harmful effects of water and toothpaste.

In the application, a labyrinth seal in the dovetail form is described as a movable seal between the ring-shaped holders. It should be noted that a labyrinth seal of another form, as well as any other known seals of movable joints complying with the requirements of simplicity and reliability can be used instead thereof.

Consequently, the inventive mechanical toothbrushes, having a sufficiently simple construction with a reliable sealing of the motor and drive elements, are developed and described hereinabove. Their tests have shown a high efficacy of these toothbrushes for tooth cleaning.

The invention claimed is:

1. A mechanical toothbrush, having a longitudinal axis, said toothbrush comprising:
    a handle;
    a neck connected to the handle;
    a head connected to the neck, the head is made in the form of a protective screen opened at one side; said protective screen includes screen butt ends;
    an even number of bristle holders capable of angular displacements in opposite directions around the longitudinal axis, said bristle holders are mounted on said head; said bristle holders are made in the form of separate rings with a radial arrangement of bristles secured thereon; said bristle holders include holder butt ends;
    a drive mechanism for driving said bristle holders, said drive mechanism is disposed substantially within said handle, said neck, and said head; the handle, the neck, and the head are sequentially disposed along the longitudinal axis; and
    a number of movable seals;
    wherein:
        said bristle holders are joined to one another and with the protective screen by means of attaching said screen butt ends to said holder butt ends via corresponding said movable seals disposed therebetween, such that said bristle holders, said protective screen, and said movable seals collectively form a body hermetically sealing the drive mechanism.

2. The mechanical toothbrush according to claim 1, wherein said bristle holders are capable of a periodic angular displacement, the bristles are mounted only in the parts of surface of said bristle holders turned to the open side of said protective screen, and said drive mechanism provides for angular oscillations of the bristle holders.

3. The mechanical toothbrush according to claim 1, wherein said bristle holders are capable of a continuous angular displacement, and said drive mechanism provides for a continuous rotational displacement of the bristle holders.

4. A mechanical toothbrush, having a longitudinal axis, said toothbrush comprising: a handle; a neck connected to the handle; a head connected to the neck, the head is made in the form of a protective screen opened at one side; a number of bristle holders capable of angular displacements in opposite directions around the longitudinal axis; a drive mechanism for providing angular oscillations of said bristle holders, said drive mechanism is disposed substantially within said handle, said neck, and said head; the handle, the neck, and the head are sequentially disposed along the longitudinal axis; wherein:
    said drive mechanism comprises:
        a motor disposed in said handle, the motor has an output shaft;
        a crank joined with the output shaft, the crank has two elbows;
        two forks arranged within said handle along the longitudinal axis, each said fork is jointed with a corresponding said elbow;
        an outer shaft and an inner shaft coaxially enclosed in said outer shaft; said outer and inner shafts extend through the handle, the neck, and the head along the longitudinal axis; said outer and inner shafts are joined with corresponding said forks; said outer and inner shafts, in portions thereof disposed within said head, are furnished with radial fingers engaged substantially with said bristle holders in the next but one order, whereas the fingers of said inner shaft extend to the corresponding bristle holders through arched holes made on the side surface of said outer shaft; and
    wherein
    the number of bristle holders is even; said bristle holders are made in the form of separate rings with a radial arrangement of bristles secured thereon; and said bristle holders are joined to one another and with the protective screen by means for sealing thereof, thereby protecting the drive mechanism from penetration of water and toothpaste therein.

5. A mechanical toothbrush, having a longitudinal axis, said toothbrush comprising: a handle; a neck connected to the handle; a head connected to the neck, the head is made in the form of a protective screen opened at one side, the head has a plurality of holes made in the side surface thereof; a number of bristle holders capable of angular displacements in opposite directions around the longitudinal axis, said bristle holders are mounted on the head inside the protective screen; a drive mechanism for providing angular rotation of said bristle holders, said drive mechanism is disposed substantially within said handle, said neck, and said head; the handle, the neck, and the head are sequentially disposed along said longitudinal axis;
    wherein:
    the number of bristle holders is even; said bristle holders are made in the form of separate rings with a radial arrangement of bristles secured thereon, said bristle holders each has an inner surface made in the form of a tooth gear wheel of inner engagement; said bristle holders are divided into uneven and even holders;
    said drive mechanism comprises:
        a motor disposed in said handle, the motor has an output shaft;
        two parallel shafts jointed substantially with said output shaft such that the shafts rotate in opposite directions;
        a plurality of pinions mounted on each of the two shafts such that the pinions of one shaft engage with said tooth gear wheels of the even holders through corresponding said holes made in the head, and the pinions of the other shaft engage with said tooth gear wheels of the uneven holders through corresponding said holes made in the head;
    and said bristle holders are joined to one another and with the protective screen by means for sealing thereof, thereby protecting the drive mechanism from penetration of water and toothpaste therein.

\* \* \* \* \*